US010959761B2

(12) United States Patent
Dekel et al.

(10) Patent No.: US 10,959,761 B2
(45) Date of Patent: Mar. 30, 2021

(54) INTRAMEDULLARY FIXATED SUBACROMIAL SPACERS

(71) Applicant: Ortho-Space Ltd., Caesarea (IL)

(72) Inventors: Assaf Dekel, Caesarea (IL); Ronny Winshtein, Caesarea (IL)

(73) Assignee: Ortho-Space Ltd.

( * ) Notice: Subject to any disclaimer, the term of this patent is extended or adjusted under 35 U.S.C. 154(b) by 134 days.

(21) Appl. No.: 15/760,824

(22) PCT Filed: Sep. 19, 2016

(86) PCT No.: PCT/IB2016/001316
§ 371 (c)(1),
(2) Date: Mar. 16, 2018

(87) PCT Pub. No.: WO2017/046647
PCT Pub. Date: Mar. 23, 2017

(65) Prior Publication Data
US 2018/0256217 A1  Sep. 13, 2018

Related U.S. Application Data

(60) Provisional application No. 62/220,771, filed on Sep. 18, 2015.

(51) Int. Cl.
*A61F 2/40* (2006.01)
*A61B 17/72* (2006.01)
(Continued)

(52) U.S. Cl.
CPC .......... *A61B 17/72* (2013.01); *A61F 2/30724* (2013.01); *A61F 2/40* (2013.01);
(Continued)

(58) Field of Classification Search
CPC ...... A61F 2/30724; A61F 2/40; A61F 2/4003; A61F 2002/4088
See application file for complete search history.

(56) References Cited

U.S. PATENT DOCUMENTS 3,631,854 A   1/1972 Fryer
3,701,771 A  10/1972 Almen et al.
(Continued)

FOREIGN PATENT DOCUMENTS

EP  0441516 A2   8/1991
EP  0617930 A1  10/1994
(Continued)

OTHER PUBLICATIONS

International Search Report and Written Opinion in International Application No. PCT/IB2016/001316, dated Jan. 30, 2017, 10 pages.
(Continued)

*Primary Examiner* — Dinah Baria
(74) *Attorney, Agent, or Firm* — Lerner, David, Littenberg, Krumholz & Mentlik, LLP (57) ABSTRACT

A prosthesis including a subacromial spacer having a surface contoured to maintain an acromion in chosen distance to a humeral head upon rotation and fixation means to fixate the subacromial spacer to a humeral medullary cavity and/or an intramedullary fixator implanted or configured for implantation in the humeral medullary cavity. A surgical kit includes the prosthesis and a proximal humeral nail. The fixating means are connectable into a proximal opening of the proximal humeral nail. A method may include: creating a percutaneous passage from an outer-body space to a portion of a humeral head; removing bony tissue to facilitate direct communication between the outer-body space and a humeral medullary cavity enclosed in the humeral head; providing a prosthesis including a subacromial spacer having a surface; and/or fixating the subacromial spacer to the humeral medullary cavity and/or an intramedullary fixator implanted or configured for implantation in the humeral medullary cavity.

15 Claims, 8 Drawing Sheets

(51) Int. Cl.
  *A61F 2/30* (2006.01)
  *A61B 17/16* (2006.01)
  *A61B 17/17* (2006.01)
(52) U.S. Cl.
  CPC ............ *A61F 2/4003* (2013.01); *A61B 17/16* (2013.01); *A61B 17/1717* (2013.01); *A61B 17/1725* (2013.01); *A61F 2002/30624* (2013.01); *A61F 2002/4088* (2013.01)

(56) References Cited

U.S. PATENT DOCUMENTS

| | | |
|---|---|---|
| 3,800,788 A | 4/1974 | White |
| 3,979,778 A | 9/1976 | Stroot |
| 4,364,392 A | 12/1982 | Strother et al. |
| 4,364,921 A | 12/1982 | Speck et al. |
| 4,638,803 A | 1/1987 | Rand |
| 4,662,883 A | 5/1987 | Bell et al. |
| 4,669,478 A | 6/1987 | Robertson |
| 4,719,918 A | 1/1988 | Bonomo et al. |
| 4,798,205 A | 1/1989 | Bonomo et al. |
| 4,892,550 A | 1/1990 | Huebsch |
| 4,906,244 A | 3/1990 | Pinchuk et al. |
| 4,932,938 A | 6/1990 | Goldberg et al. |
| 4,932,956 A | 6/1990 | Reddy et al. |
| 4,932,958 A | 6/1990 | Reddy et al. |
| 5,002,556 A | 3/1991 | Ishida et al. |
| 5,021,043 A | 6/1991 | Becker et al. |
| 5,033,481 A | 7/1991 | Heyler, III |
| 5,071,410 A | 12/1991 | Pazell |
| 5,071,429 A | 12/1991 | Pinchuk et al. |
| 5,102,413 A | 4/1992 | Poddar |
| 5,122,113 A | 6/1992 | Hattler |
| 5,163,949 A | 11/1992 | Bonutti |
| 5,163,950 A | 11/1992 | Pinchuk et al. |
| 5,176,698 A | 1/1993 | Burns et al. |
| 5,181,921 A | 1/1993 | Makita et al. |
| 5,222,970 A | 6/1993 | Reeves |
| 5,295,994 A | 3/1994 | Bonutti |
| 5,314,479 A * | 5/1994 | Rockwood, Jr. .......... A61F 2/40 623/19.14 |
| 5,331,975 A | 7/1994 | Bonutti |
| 5,344,451 A | 9/1994 | Dayton |
| 5,344,459 A | 9/1994 | Swartz |
| 5,370,691 A | 12/1994 | Samson |
| 5,423,850 A | 6/1995 | Berger |
| 5,425,357 A | 6/1995 | Moll et al. |
| 5,468,245 A | 11/1995 | Vargas, III |
| 5,480,400 A | 1/1996 | Berger |
| 5,507,770 A | 4/1996 | Turk |
| 5,514,153 A | 5/1996 | Bonutti |
| 5,524,633 A | 6/1996 | Heaven et al. |
| 5,549,625 A | 8/1996 | Bircoll |
| 5,571,179 A | 11/1996 | Manders et al. |
| 5,575,759 A | 11/1996 | Moll et al. |
| 5,632,762 A | 5/1997 | Myler |
| 5,645,560 A | 7/1997 | Crocker et al. |
| 5,658,310 A | 8/1997 | Berger |
| 5,658,329 A | 8/1997 | Purkait |
| 5,662,712 A | 9/1997 | Pathak et al. |
| 5,667,520 A | 9/1997 | Bonutti |
| 5,683,405 A | 11/1997 | Yacoubian et al. |
| 5,704,893 A | 1/1998 | Timm |
| 5,720,762 A | 2/1998 | Bass |
| 5,725,568 A | 3/1998 | Hastings |
| 5,746,762 A | 5/1998 | Bass |
| 5,746,763 A | 5/1998 | Benderev et al. |
| 5,779,672 A | 7/1998 | Dormandy, Jr. |
| 5,779,728 A | 7/1998 | Lunsford et al. |
| 5,798,096 A | 8/1998 | Pavlyk |
| 5,823,995 A | 10/1998 | Fitzmaurice et al. |
| 5,827,289 A | 10/1998 | Reiley et al. |
| 5,827,318 A | 10/1998 | Bonutti |
| 5,843,116 A | 12/1998 | Crocker et al. |
| 5,860,997 A | 1/1999 | Bonutti |
| 5,871,537 A | 2/1999 | Holman et al. |
| 5,888,196 A | 3/1999 | Bonutti |
| 5,925,058 A | 7/1999 | Smith et al. |
| 5,935,667 A | 8/1999 | Calcote et al. |
| 5,941,909 A | 8/1999 | Purkait |
| 5,954,739 A | 9/1999 | Bonutti |
| 5,968,068 A | 10/1999 | Dehdashtian et al. |
| 5,971,992 A | 10/1999 | Solar |
| 5,972,015 A | 10/1999 | Scribner et al. |
| 5,979,452 A | 11/1999 | Fogarty et al. |
| 5,984,942 A | 11/1999 | Alden et al. |
| 6,017,305 A | 1/2000 | Bonutti |
| 6,018,094 A | 1/2000 | Fox |
| 6,027,486 A | 2/2000 | Crocker et al. |
| 6,027,517 A | 2/2000 | Crocker et al. |
| 6,036,640 A | 3/2000 | Corace et al. |
| 6,042,596 A | 3/2000 | Bonutti |
| 6,066,154 A | 5/2000 | Reiley et al. |
| 6,068,626 A | 5/2000 | Harrington et al. |
| 6,074,341 A | 6/2000 | Anderson et al. |
| 6,099,547 A | 8/2000 | Gellman et al. |
| 6,106,541 A | 8/2000 | Hurbis |
| 6,117,165 A | 9/2000 | Becker |
| 6,120,523 A | 9/2000 | Crocker et al. |
| 6,171,236 B1 | 1/2001 | Bonutti |
| 6,186,978 B1 | 2/2001 | Samson et al. |
| 6,187,023 B1 | 2/2001 | Bonutti |
| 6,235,043 B1 | 5/2001 | Reiley et al. |
| 6,240,924 B1 | 6/2001 | Fogarty et al. |
| 6,248,110 B1 | 6/2001 | Reiley et al. |
| 6,248,131 B1 | 6/2001 | Felt et al. |
| 6,280,456 B1 | 8/2001 | Scribner et al. |
| 6,280,457 B1 | 8/2001 | Wallace et al. |
| 6,293,960 B1 | 9/2001 | Ken |
| 6,306,081 B1 | 10/2001 | Ishikawa et al. |
| 6,306,177 B1 | 10/2001 | Felt et al. |
| 6,312,462 B1 | 11/2001 | McDermott et al. |
| 6,331,191 B1 | 12/2001 | Chobotov |
| 6,352,551 B1 | 3/2002 | Wang |
| 6,379,329 B1 | 4/2002 | Naglreiter et al. |
| 6,391,538 B1 | 5/2002 | Vyavahare et al. |
| 6,395,019 B2 | 5/2002 | Chobotov |
| 6,395,208 B1 | 5/2002 | Herweck et al. |
| 6,409,741 B1 | 6/2002 | Crocker et al. |
| 6,409,749 B1 | 6/2002 | Maynard |
| 6,419,701 B1 | 7/2002 | Cook et al. |
| 6,423,032 B2 | 7/2002 | Parodi |
| 6,423,083 B2 | 7/2002 | Reiley et al. |
| 6,443,941 B1 | 9/2002 | Slepian et al. |
| 6,451,042 B1 | 9/2002 | Bonutti |
| 6,500,190 B2 | 12/2002 | Greene, Jr. et al. |
| 6,503,265 B1 | 1/2003 | Fogarty et al. |
| 6,530,878 B2 | 3/2003 | Silverman et al. |
| 6,533,799 B1 | 3/2003 | Bouchier |
| 6,547,767 B1 | 4/2003 | Moein |
| 6,591,838 B2 | 7/2003 | Durgin |
| 6,599,275 B1 | 7/2003 | Fischer, Jr. |
| 6,607,544 B1 | 8/2003 | Boucher et al. |
| 6,616,673 B1 | 9/2003 | Stone et al. |
| 6,620,181 B1 | 9/2003 | Bonutti |
| 6,620,197 B2 * | 9/2003 | Maroney .................. A61F 2/40 623/19.14 |
| 6,623,505 B2 | 9/2003 | Scribner et al. |
| 6,632,235 B2 | 10/2003 | Weikel et al. |
| 6,652,587 B2 | 11/2003 | Felt et al. |
| 6,663,647 B2 | 12/2003 | Reiley et al. |
| 6,668,836 B1 | 12/2003 | Greenburg et al. |
| 6,706,064 B1 | 3/2004 | Anson |
| 6,716,216 B1 | 4/2004 | Boucher et al. |
| 6,719,773 B1 | 4/2004 | Boucher et al. |
| 6,746,465 B2 | 6/2004 | Diederich et al. |
| 6,837,850 B2 | 1/2005 | Suddaby |
| 6,860,892 B1 | 3/2005 | Tanaka et al. |
| 6,872,215 B2 | 3/2005 | Crocker et al. |
| 6,899,719 B2 | 5/2005 | Reiley et al. |
| 6,958,212 B1 | 10/2005 | Hubbell et al. |
| 6,979,341 B2 | 12/2005 | Scribner et al. |
| 6,981,980 B2 | 1/2006 | Sampson et al. |
| 6,981,981 B2 | 1/2006 | Reiley et al. |

(56) References Cited

U.S. PATENT DOCUMENTS

| | | |
|---|---|---|
| 7,001,431 B2 | 2/2006 | Bao et al. |
| 7,029,487 B2 | 4/2006 | Greene, Jr. et al. |
| 7,044,954 B2 | 5/2006 | Reiley et al. |
| 7,044,978 B2 | 5/2006 | Howie et al. |
| 7,060,100 B2 | 6/2006 | Ferree et al. |
| 7,156,860 B2 | 1/2007 | Wallsten |
| 7,156,861 B2 | 1/2007 | Scribner et al. |
| 7,160,325 B2 | 1/2007 | Morningstar |
| 7,166,121 B2 | 1/2007 | Reiley et al. |
| 7,201,762 B2 | 4/2007 | Greene, Jr. et al. |
| 7,217,273 B2 | 5/2007 | Bonutti |
| 7,226,481 B2 | 6/2007 | Kuslich |
| 7,241,303 B2 | 7/2007 | Reiss et al. |
| 7,261,720 B2 | 8/2007 | Stevens et al. |
| 7,320,709 B2 | 1/2008 | Felt et al. |
| 7,368,124 B2 | 5/2008 | Chun et al. |
| 7,476,235 B2 | 1/2009 | Diederich et al. |
| 7,488,337 B2 | 2/2009 | Saab et al. |
| 7,583,520 B2 | 9/2009 | Aso |
| 7,589,980 B2 | 9/2009 | Aso |
| 7,632,291 B2 | 12/2009 | Stephens et al. |
| 7,695,488 B2 | 4/2010 | Berenstein et al. |
| 7,699,894 B2 | 4/2010 | O'Neil et al. |
| 7,749,267 B2 | 7/2010 | Karmon |
| 7,799,077 B2 | 9/2010 | Lang et al. |
| 7,819,881 B2 | 10/2010 | Stone et al. |
| 8,277,511 B2 | 10/2012 | Tornier et al. |
| 8,317,865 B2 | 11/2012 | Osorio et al. |
| 8,328,875 B2 | 12/2012 | Linares |
| 8,377,135 B1 | 2/2013 | McLeod et al. |
| 8,500,815 B2 | 8/2013 | Fockens |
| 8,512,347 B2 | 8/2013 | McCormack et al. |
| 8,556,971 B2 | 10/2013 | Lang |
| 8,632,601 B2 | 1/2014 | Howald et al. |
| 8,753,390 B2 | 6/2014 | Shohat |
| 8,771,363 B2 | 7/2014 | Grotz |
| 8,894,713 B2 | 11/2014 | Shohat et al. |
| 8,926,622 B2 | 1/2015 | McKay |
| 9,132,015 B2 | 9/2015 | Bromer |
| 9,271,779 B2 | 3/2016 | Bonutti |
| 9,289,307 B2 | 3/2016 | Shohat |
| 9,345,577 B2 | 5/2016 | Vanleeuwen et al. |
| 9,408,709 B2 | 8/2016 | Wirtel, III et al. |
| 9,533,024 B2 | 1/2017 | Sevrain et al. |
| 9,545,316 B2 | 1/2017 | Ashley et al. |
| 9,545,321 B2 | 1/2017 | Hibri et al. |
| 9,585,761 B2 | 3/2017 | Teisen et al. |
| 9,622,873 B2 | 4/2017 | McCormack |
| 9,687,353 B2 | 6/2017 | Afzal |
| 9,750,534 B2 | 9/2017 | Philippon et al. |
| 9,750,611 B2 | 9/2017 | Fell |
| 9,757,241 B2 | 9/2017 | Grotz |
| 9,770,337 B2 | 9/2017 | Shohat |
| 9,808,345 B2 | 11/2017 | Grotz |
| 9,949,838 B2 | 4/2018 | Vanleeuwen et al. |
| 10,004,605 B2 | 6/2018 | Grotz |
| 2001/0008976 A1 | 7/2001 | Wang |
| 2001/0011174 A1 | 8/2001 | Reiley et al. |
| 2001/0049531 A1 | 12/2001 | Reiley et al. |
| 2002/0013600 A1 | 1/2002 | Scribner et al. |
| 2002/0026195 A1 | 2/2002 | Layne et al. |
| 2002/0082608 A1 | 6/2002 | Reiley et al. |
| 2002/0127264 A1 | 9/2002 | Felt et al. |
| 2002/0143402 A1 | 10/2002 | Steinberg |
| 2002/0156489 A1 | 10/2002 | Gellman et al. |
| 2002/0161388 A1 | 10/2002 | Samuels et al. |
| 2002/0165570 A1 | 11/2002 | Mollenauer et al. |
| 2002/0173852 A1 | 11/2002 | Felt et al. |
| 2002/0177866 A1 | 11/2002 | Weikel et al. |
| 2002/0183778 A1 | 12/2002 | Reiley et al. |
| 2002/0183850 A1 | 12/2002 | Felt et al. |
| 2003/0018352 A1 | 1/2003 | Mollenauer et al. |
| 2003/0018388 A1 | 1/2003 | Comer |
| 2003/0023260 A1 | 1/2003 | Bonutti |
| 2003/0028211 A1 | 2/2003 | Crocker et al. |
| 2003/0032963 A1 | 2/2003 | Reiss et al. |
| 2003/0033017 A1 | 2/2003 | Lotz et al. |
| 2003/0036797 A1 | 2/2003 | Malaviya et al. |
| 2003/0074084 A1 | 4/2003 | Nakao |
| 2003/0093107 A1 | 5/2003 | Parsonage et al. |
| 2003/0114878 A1 | 6/2003 | Diederich et al. |
| 2003/0114934 A1 | 6/2003 | Steinberg |
| 2003/0130664 A1 | 7/2003 | Boucher et al. |
| 2003/0135211 A1* | 7/2003 | Cho .................. A61B 17/1725 606/62 |
| 2003/0147935 A1 | 8/2003 | Binette et al. |
| 2003/0181800 A1 | 9/2003 | Bonutti |
| 2003/0191489 A1 | 10/2003 | Reiley et al. |
| 2003/0195547 A1 | 10/2003 | Scribner et al. |
| 2003/0212426 A1 | 11/2003 | Olson et al. |
| 2003/0216776 A1 | 11/2003 | Mollenauer et al. |
| 2003/0220648 A1 | 11/2003 | Osorio et al. |
| 2003/0229372 A1 | 12/2003 | Reiley et al. |
| 2003/0236513 A1 | 12/2003 | Schwarz et al. |
| 2004/0010263 A1 | 1/2004 | Boucher et al. |
| 2004/0093008 A1 | 5/2004 | Zamore |
| 2004/0097794 A1 | 5/2004 | Bonutti |
| 2004/0097949 A1 | 5/2004 | Bonutti |
| 2004/0098015 A1 | 5/2004 | Weikel et al. |
| 2004/0098016 A1 | 5/2004 | Bonutti |
| 2004/0098017 A1 | 5/2004 | Saab et al. |
| 2004/0107000 A1 | 6/2004 | Felt et al. |
| 2004/0117019 A1 | 6/2004 | Trieu et al. |
| 2004/0127930 A1 | 7/2004 | Bonutti |
| 2004/0133276 A1 | 7/2004 | Lang et al. |
| 2004/0138689 A1 | 7/2004 | Bonutti |
| 2004/0138690 A1 | 7/2004 | Bonutti |
| 2004/0143285 A1 | 7/2004 | Bonutti |
| 2004/0147811 A1 | 7/2004 | Diederich et al. |
| 2004/0153114 A1 | 8/2004 | Reiley et al. |
| 2004/0153115 A1 | 8/2004 | Reiley et al. |
| 2004/0167561 A1 | 8/2004 | Boucher et al. |
| 2004/0167562 A1 | 8/2004 | Osorio et al. |
| 2004/0167563 A1 | 8/2004 | Fogarty et al. |
| 2004/0175408 A1 | 9/2004 | Chun et al. |
| 2004/0186504 A1 | 9/2004 | Schulter et al. |
| 2004/0220669 A1 | 11/2004 | Studer |
| 2004/0230218 A1 | 11/2004 | Criscuolo et al. |
| 2004/0236425 A1 | 11/2004 | Huang |
| 2004/0243170 A1 | 12/2004 | Suresh et al. |
| 2004/0247641 A1 | 12/2004 | Felt et al. |
| 2005/0015140 A1 | 1/2005 | deBeer |
| 2005/0015154 A1 | 1/2005 | Lindsey et al. |
| 2005/0043808 A1 | 2/2005 | Felt et al. |
| 2005/0090852 A1 | 4/2005 | Layne et al. |
| 2005/0113937 A1 | 5/2005 | Binette et al. |
| 2005/0113938 A1 | 5/2005 | Jamiolkowski et al. |
| 2005/0119662 A1 | 6/2005 | Reiley et al. |
| 2005/0123581 A1 | 6/2005 | Ringeisen et al. |
| 2005/0131267 A1 | 6/2005 | Talmadge |
| 2005/0131268 A1 | 6/2005 | Talmadge |
| 2005/0131269 A1 | 6/2005 | Talmadge |
| 2005/0143836 A1 | 6/2005 | Steinberg |
| 2005/0177244 A1 | 8/2005 | Steinberg |
| 2005/0209629 A1 | 9/2005 | Kerr et al. |
| 2005/0229433 A1 | 10/2005 | Cachia |
| 2005/0234498 A1 | 10/2005 | Gronemeyer et al. |
| 2005/0245961 A1 | 11/2005 | Mollenauer et al. |
| 2005/0251195 A1 | 11/2005 | Wang |
| 2005/0261722 A1 | 11/2005 | Crocker et al. |
| 2006/0064169 A1 | 3/2006 | Ferree |
| 2006/0069403 A1 | 3/2006 | Shalon et al. |
| 2006/0085022 A1 | 4/2006 | Hayes et al. |
| 2006/0085023 A1 | 4/2006 | Davies et al. |
| 2006/0085024 A1 | 4/2006 | Pepper et al. |
| 2006/0085080 A1 | 4/2006 | Bechgaard et al. |
| 2006/0095064 A1 | 5/2006 | Scribner et al. |
| 2006/0149380 A1 | 7/2006 | Lotz et al. |
| 2006/0173484 A1 | 8/2006 | Solomon |
| 2006/0229631 A1 | 10/2006 | Reiley et al. |
| 2006/0235460 A1 | 10/2006 | Reiley et al. |
| 2006/0241765 A1 | 10/2006 | Burn et al. |
| 2006/0276819 A1 | 12/2006 | Osorio et al. |
| 2006/0287665 A1 | 12/2006 | Burton et al. |

(56) References Cited

U.S. PATENT DOCUMENTS

| | | |
|---|---|---|
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0021769 A1 | 1/2007 | Scribner et al. |
| 2007/0049961 A1 | 3/2007 | Tsou et al. |
| 2007/0055300 A1 | 3/2007 | Osorio et al. |
| 2007/0060941 A1 | 3/2007 | Reiley et al. |
| 2007/0078477 A1 | 4/2007 | Heneveld et al. |
| 2007/0118171 A1 | 5/2007 | Reiley et al. |
| 2007/0162067 A1 | 7/2007 | Lunsford et al. |
| 2007/0167973 A1 | 7/2007 | Stupecky et al. |
| 2007/0186939 A1 | 8/2007 | Farmache |
| 2007/0190108 A1 | 8/2007 | Datta et al. |
| 2007/0213760 A1 | 9/2007 | Hayes et al. |
| 2007/0225705 A1 | 9/2007 | Osorio et al. |
| 2007/0225810 A1 | 9/2007 | Colleran et al. |
| 2007/0299455 A1 | 12/2007 | Stevens et al. |
| 2007/0299460 A9 | 12/2007 | Boucher et al. |
| 2008/0004596 A1 | 1/2008 | Yun et al. |
| 2008/0015626 A1 | 1/2008 | Keith et al. |
| 2008/0027470 A1 | 1/2008 | Hart et al. |
| 2008/0045994 A1 | 2/2008 | Rehnke |
| 2008/0051818 A1 | 2/2008 | Phan et al. |
| 2008/0051819 A1 | 2/2008 | Chasmawala et al. |
| 2008/0051825 A1 | 2/2008 | Reiley et al. |
| 2008/0058823 A1 | 3/2008 | Reiley et al. |
| 2008/0058824 A1 | 3/2008 | Reiley et al. |
| 2008/0058828 A1 | 3/2008 | Reiley et al. |
| 2008/0058855 A1 | 3/2008 | Reiley et al. |
| 2008/0058857 A1 | 3/2008 | Reiley et al. |
| 2008/0058943 A1 | 3/2008 | Reiley et al. |
| 2008/0065089 A1 | 3/2008 | Osorio et al. |
| 2008/0065137 A1 | 3/2008 | Boucher et al. |
| 2008/0065138 A1 | 3/2008 | Reiley et al. |
| 2008/0065139 A1 | 3/2008 | Scribner et al. |
| 2008/0065142 A1 | 3/2008 | Reiley et al. |
| 2008/0065143 A1 | 3/2008 | Reiley et al. |
| 2008/0065190 A1 | 3/2008 | Osorio et al. |
| 2008/0071385 A1 | 3/2008 | Binette et al. |
| 2008/0086133 A1 | 4/2008 | Kuslich et al. |
| 2008/0103518 A1 | 5/2008 | Karmon |
| 2008/0132934 A1 | 6/2008 | Reiley et al. |
| 2008/0132935 A1 | 6/2008 | Osorio et al. |
| 2008/0140079 A1 | 6/2008 | Osorio et al. |
| 2008/0140083 A1 | 6/2008 | Reiley et al. |
| 2008/0140084 A1 | 6/2008 | Osorio et al. |
| 2008/0154233 A1 | 6/2008 | Yao et al. |
| 2008/0172081 A1 | 7/2008 | Reiss et al. |
| 2008/0195112 A1 | 8/2008 | Liu et al. |
| 2008/0195207 A1 | 8/2008 | Lin et al. |
| 2008/0200989 A1 | 8/2008 | Cachia |
| 2008/0215031 A1 | 9/2008 | Belfort et al. |
| 2008/0221608 A1 | 9/2008 | Betts |
| 2008/0221628 A1 | 9/2008 | Milbocker et al. |
| 2008/0234820 A1 | 9/2008 | Felt et al. |
| 2008/0241213 A1 | 10/2008 | Chun et al. |
| 2008/0243122 A1 | 10/2008 | Kohm et al. |
| 2008/0249529 A1 | 10/2008 | Zarda et al. |
| 2008/0249603 A1 | 10/2008 | Schwardt et al. |
| 2008/0249604 A1 | 10/2008 | Donovan et al. |
| 2008/0255569 A1 | 10/2008 | Kohm et al. |
| 2008/0255624 A1 | 10/2008 | Arcenio et al. |
| 2008/0269748 A1 | 10/2008 | Justin et al. |
| 2008/0269759 A1 | 10/2008 | Reiley et al. |
| 2008/0269795 A1 | 10/2008 | Reiley et al. |
| 2008/0269796 A1 | 10/2008 | Reiley et al. |
| 2008/0275483 A1 | 11/2008 | Makower et al. |
| 2008/0281355 A1 | 11/2008 | Mayer et al. |
| 2008/0294187 A1 | 11/2008 | Krisht |
| 2008/0294205 A1 | 11/2008 | Greenhalgh et al. |
| 2008/0300604 A1 | 12/2008 | Lu et al. |
| 2009/0012618 A1 | 1/2009 | Ahrens et al. |
| 2009/0037148 A1 | 2/2009 | Lin et al. |
| 2009/0043344 A1 | 2/2009 | Schlotterback |
| 2009/0048623 A1 | 2/2009 | Lafosse et al. |
| 2009/0048684 A1 | 2/2009 | Lesh |
| 2009/0062871 A1 | 3/2009 | Chin et al. |
| 2009/0076318 A1 | 3/2009 | Li |
| 2009/0076517 A1 | 3/2009 | Reiley et al. |
| 2009/0082872 A1 | 3/2009 | Beger |
| 2009/0082874 A1 | 3/2009 | Cachia |
| 2009/0088788 A1 | 4/2009 | Mouw |
| 2009/0088789 A1 | 4/2009 | O'Neil et al. |
| 2009/0088846 A1 | 4/2009 | Myung et al. |
| 2009/0101157 A1 | 4/2009 | Karmon |
| 2009/0104586 A1 | 4/2009 | Cardoso et al. |
| 2009/0105527 A1 | 4/2009 | Connors et al. |
| 2009/0105732 A1 | 4/2009 | Yurek et al. |
| 2009/0105745 A1 | 4/2009 | Culbert |
| 2009/0112214 A1 | 4/2009 | Philippon et al. |
| 2009/0131952 A1 | 5/2009 | Schumacher et al. |
| 2009/0157084 A1 | 6/2009 | Aalsma et al. |
| 2009/0157087 A1 | 6/2009 | Wei et al. |
| 2009/0177206 A1 | 7/2009 | Lozier et al. |
| 2009/0182368 A1 | 7/2009 | Lunsford et al. |
| 2009/0201700 A1 | 8/2009 | Aso et al. |
| 2009/0234457 A1 | 9/2009 | Lotz et al. |
| 2010/0082036 A1 | 4/2010 | Reiley et al. |
| 2010/0114318 A1 | 5/2010 | Gittings et al. |
| 2010/0137923 A1 | 6/2010 | Greenhalgh et al. |
| 2010/0168755 A1 | 7/2010 | Reiley et al. |
| 2010/0292798 A1 | 11/2010 | Maestretti |
| 2011/0054408 A1 | 3/2011 | Wei et al. |
| 2011/0082552 A1 | 4/2011 | Wistrom et al. |
| 2011/0125158 A1 | 5/2011 | Diwan et al. |
| 2011/0144688 A1 | 6/2011 | Reiss et al. |
| 2011/0270393 A1 | 11/2011 | Marvel |
| 2011/0295370 A1 | 12/2011 | Suh et al. |
| 2011/0295379 A1 | 12/2011 | Shohat |
| 2012/0316645 A1 | 12/2012 | Grotz |
| 2013/0018479 A1 | 1/2013 | Grotz |
| 2013/0116794 A1 | 5/2013 | Shohat et al. |
| 2013/0325128 A1 | 12/2013 | Perloff et al. |
| 2013/0331946 A1 | 12/2013 | Shohat |
| 2014/0031939 A1 | 1/2014 | Wolfe et al. |
| 2014/0052250 A1 | 2/2014 | Wirtel, III et al. |
| 2014/0058432 A1 | 2/2014 | Scribner et al. |
| 2014/0066939 A1 | 3/2014 | Kaiser et al. |
| 2014/0128978 A1 | 5/2014 | Suh et al. |
| 2014/0142710 A1 | 5/2014 | Lang |
| 2014/0296987 A1 | 10/2014 | Shohat |
| 2014/0303730 A1 | 10/2014 | McGuire et al. |
| 2014/0303743 A1* | 10/2014 | Choudhury ............... A61F 2/34 623/22.24 |
| 2014/0343675 A1 | 11/2014 | Vanleeuwen et al. |
| 2014/0378980 A1 | 12/2014 | Lomeli et al. |
| 2015/0127104 A1 | 5/2015 | Levy et al. |
| 2015/0289988 A1 | 10/2015 | Ashley et al. |
| 2015/0320570 A1 | 11/2015 | Suh et al. |
| 2015/0351914 A1 | 12/2015 | Bromer |
| 2016/0058548 A1 | 3/2016 | Grotz |
| 2016/0095706 A1 | 4/2016 | Grotz |
| 2016/0120654 A1 | 5/2016 | Hibri et al. |
| 2016/0199197 A1 | 7/2016 | Wolfe et al. |
| 2016/0235443 A1 | 8/2016 | Kaiser et al. |
| 2016/0310286 A1 | 10/2016 | McJunkin |
| 2016/0354182 A1 | 12/2016 | Karmon |
| 2017/0042698 A1 | 2/2017 | Saidha et al. |
| 2017/0119535 A1 | 5/2017 | Teisen et al. |
| 2017/0312088 A1 | 11/2017 | Grotz |
| 2018/0000603 A1 | 1/2018 | Shohat |
| 2018/0028319 A1 | 2/2018 | Grotz |
| 2018/0028326 A1 | 2/2018 | Vanleeuwen et al. |

FOREIGN PATENT DOCUMENTS

| | | |
|---|---|---|
| EP | 1635738 A2 | 3/2006 |
| WO | 9425078 A1 | 11/1994 |
| WO | 9640023 A1 | 12/1996 |
| WO | 9640024 A1 | 12/1996 |
| WO | 9719653 A1 | 6/1997 |
| WO | 9826737 A1 | 6/1998 |
| WO | 9903454 A1 | 1/1999 |
| WO | 9915116 A1 | 4/1999 |

(56) References Cited

FOREIGN PATENT DOCUMENTS

| WO | 0013624 A2 | 3/2000 |
| WO | 0044808 A1 | 8/2000 |
| WO | 0113832 A1 | 3/2001 |
| WO | 0113833 A1 | 3/2001 |
| WO | 03105917 A2 | 12/2003 |
| WO | 2004112656 A2 | 12/2004 |

OTHER PUBLICATIONS

International Preliminary Report on Patentability in International Application No. PCT/IB2016/001316, dated Mar. 20, 2018, 8 pages.

\* cited by examiner

INTRAMEDULLARY FIXATED SUBACROMIAL SPACERS

CROSS-REFERENCE TO RELATED APPLICATIONS

This application is a National Stage Application under 35 U.S.C. 071 and claims the benefit of International Application No. PCT/IB2016/001316, filed Sep. 19, 2016, which claims the benefit of U.S. Application Ser. No. 62/220,771 entitled "INTERAMEDULLARY FIXATED SUBACROMIAL SPACERS" and filed on Sep. 18, 2015, which is are hereby incorporated by reference in their entirety.

TECHNICAL FIELD

The present invention, in some embodiments thereof, relates to shoulder implants, and in particular to prostheses for spacing acromion and humeral head in a shoulder.

BACKGROUND

Figure 1:
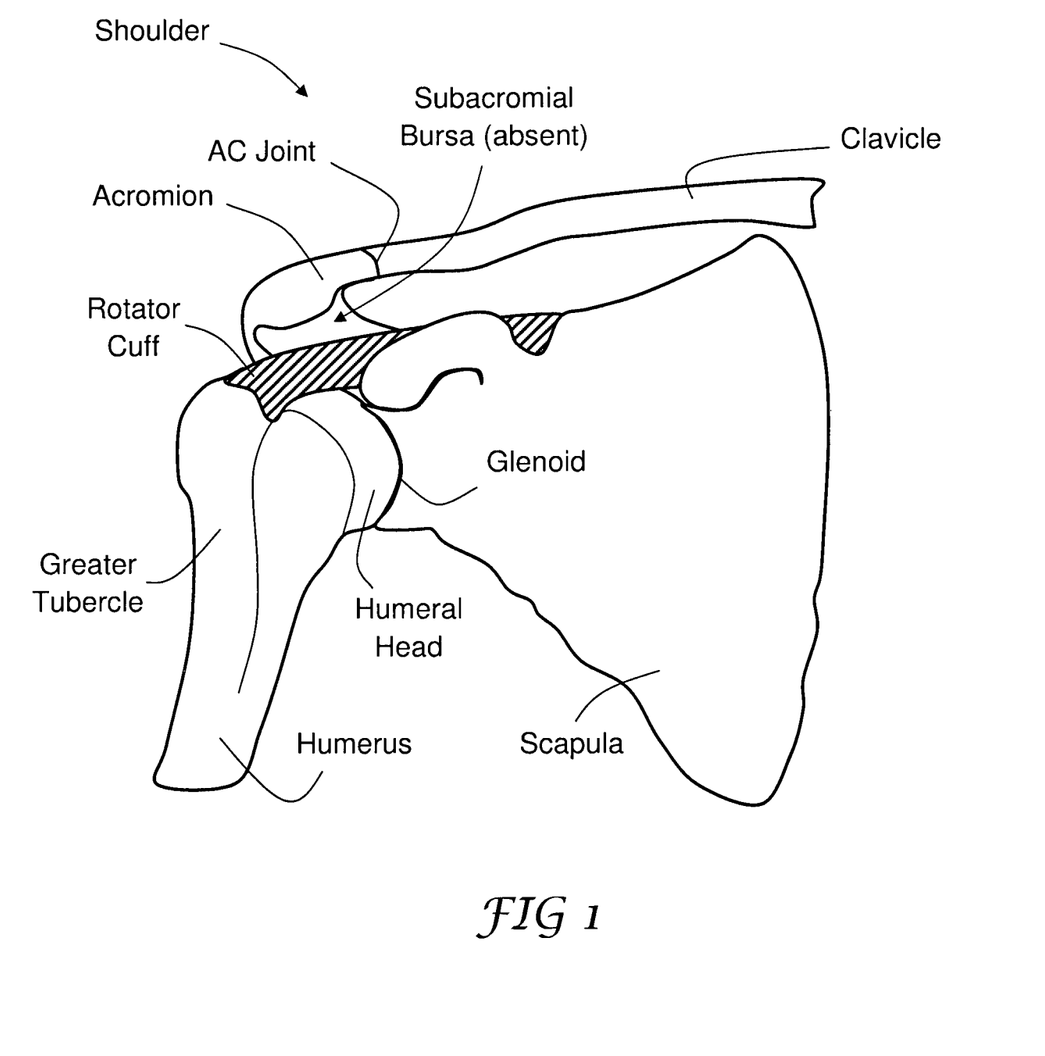
FIG. 1 schematically illustrates a portion of a human shoulder anatomy.

The human shoulder has many degrees of freedom and a unique mechanism for stabilization at rest. FIG. 1 schematically illustrates a portion of a human shoulder anatomy. The shoulder girdle consists of the scapula and the clavicle, and along with the humerus (upper arm bone), they form the framework of the shoulder. The upper end or head of the humerus (the humeral head) is hemisphere-like and is adjacent to two bony prominences, the greater and lesser tuberosities (tubercles). The clavicle extends from the base of the neck to the shoulder and is connected laterally to the acromion of the scapula, at the acromioclavicular (AC) joint.

Rotation of the humerus is accomplished by a group of four muscles, subscapularis, supraspinatus, infraspinatus, and teres minor, collectively called the rotator cuff. These muscles originate on different parts of the scapula, and insert like a cuff around the perimeter of the humeral head, where their tendons blend with the joint capsule. In addition to externally and internally rotating the humerus, the rotator cuff helps stabilize the joint during abduction by pulling the humeral head into the glenoid fossa. The rotator cuff stabilizes the humeral head by contrasting the action exerted by the deltoid muscle. In case of a severe damage of the rotator cuff (for example, a complete tear), the humeral head tends to migrate upwards, and a consequent subacromial impingement takes place in which the humeral head scrapes the acromion at motion, therefore creating limitation and/or pain associated with arm motions, such as arm abduction.

There are number of bursae in the region of the shoulder, each is a fluid-filled saclike cavity situated in between tissues where friction would otherwise occur. The subacromial bursa is located between the acromion and the joint capsule and is commonly involved in pathology. Ill, non-functional or absent subacromial bursa may cause direct contact between bone parts (e.g., between humeral head and acromion) and/or between soft and hard tissues (e.g., between the rotator cuff and the acromion) in ways that may result in damage to soft and perhaps hard tissues, hindered and limited motion, and pain.

SUMMARY

According to an aspect of some embodiments of the present invention there is provided a prosthesis which includes a subacromial spacer. In some embodiments the subacromial spacer includes a surface contoured to maintain an acromion in chosen distance to a humeral head upon rotation. Optionally, the chosen distance is maintained particularly during and following a shoulder full range of motion. In some embodiments, the full range of motion includes abduction to a substantial transverse position followed by an adduction to a substantial medial position.

In some embodiments, the prosthesis further including fixation means to fixate the subacromial spacer to a humeral medullary cavity and/or to an intramedullary fixator implanted or configured for implantation in the humeral medullary cavity. In some embodiments, the fixating means includes an elongated member sized to snugly fit in the medullary cavity or a slightly reamed segment in the medullary cavity.

In some embodiments, the subacromial spacer includes at least two hingedly connected parts, optionally making an articulation mechanism configured to allow relative motion in at least one axis. Optionally, the articulation mechanism is a bipolar articulation.

In an aspect of some embodiments, there is provided a surgical kit, including the prosthesis and a proximal humeral nail. In some embodiments, the fixating means are connectable into a proximal opening of the proximal humeral nail.

In an aspect of some embodiments, there is provided a method including at least one of the following steps (not necessarily in same order): creating a percutaneous passage from an outer-body space to a portion of a humeral head; removing bony tissue to facilitate direct communication between the outer-body space and a humeral medullary cavity enclosed in the humeral head; providing a prosthesis including a subacromial spacer having a surface; and fixating the subacromial spacer to the humeral medullary cavity and/or to an intramedullary fixator implanted or configured for implantation in the humeral medullary cavity.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The following preferred embodiments may be described in the context of exemplary humerus and/or subacromial space related surgical procedures for ease of description and understanding. However, the invention is not limited to the specifically described devices and methods, and may be adapted to various clinical applications without departing from the overall scope of the invention. For example, devices and related methods including concepts described herein may be used for other orthopaedic surgical procedures such as but not limited to: hip, ankle, long bones and short bones.

It is understood that the invention is not limited to the particular methodology, protocols, and reagents, etc., described herein, as these may vary as the skilled artisan will recognize. Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

The present invention, in some embodiments thereof, relates to shoulder implants, and in particular to prostheses for spacing acromion and humeral head in a shoulder.

An aspect of some embodiments of the present invention relates to a prosthesis including a subacromial spacer. In some embodiments, the subacromial spacer is at least partially rigid, and optionally at least partially formed of a biocompatible material, such as a plastic, polymer, metal alloy, ceramic or others. Optionally, the subacromial spacer includes parts or portions made of stainless steel and/or titanium alloy. Optionally, alternatively or additionally, the subacromial spacer includes a resilient portion, which is, optionally, malleable, elastic or plastic, expandable, compressible and/or stretchable. In some embodiments, the resilient portion includes a contact surface with the acromion. Optionally, the resilient portion is substantially compressive only above a predetermined threshold, optionally switching between a first mode, in which a first greater distance is maintained between the humeral head and the acromion, and a second mode, in which the distance is decreased while optionally resisting compression while creating a cushioning effect.

In some embodiments, the subacromial spacer comprises at least two hingedly connected parts, optionally making an articulation mechanism configured to allow relative motion in at least one axis, optionally at least two axes. Optionally, the articulation mechanism is a bipolar or a dual articulation, optionally self-centering, optionally uses primary internal articulation to reduce secondary acetabular articulation and associated acetabular wear.

In some embodiments, the subacromial spacer comprises a surface contoured to maintain an acromion in chosen distance to a humeral head. Optionally, such a chosen distance or a chosen range of distances is maintained at rest and/or upon rotation of the humeral head, particularly but not only during and/or following a shoulder range of motion, optionally a full range of motion. Optionally, the full range of motion includes, at least, an abduction to a substantial transverse position, optionally followed by an adduction to a substantial medial position. In this disclosure, "abduction" refers to moving of a body part away from the central axis of the body; "adduction" refers to moving of a body part toward the central axis of the body; and "medial" refers to being in or directed toward the midline or medial plane of the body. A normal shoulder range of motion may include at least one of flexion (optionally 0 to 90°), extension (optionally 0 to 50°), abduction (optionally 0 to 90°), adduction (optionally 90 to 0°), lateral rotation (optionally 0 to 90°) and medial rotation (optionally 0 to 90°).

In some embodiments, the surface of the subacromial spacer described above is smooth and allowing unhindered slippery motion with the acromion. Optionally, the surface is in contact with the acromion during an entire normal or full range of motion. The surface may be contoured such to maintain cam-like mechanical interaction between the humeral head and the acromion, while keeping a chosen or a normal variable distance between the humeral head and the acromion (e.g., by filling the void created therebetween) as the superior portion of the humeral head changes position. In some embodiments, the surface includes at least two portions, wherein a first portion is in contact with the acromion when the shoulder is at abduction, and wherein a second portion is in contact with the acromion when the shoulder is at adduction.

In some embodiments, the prosthesis also includes fixation means. In some embodiments, the fixation means are configured to fixate the subacromial spacer to a humeral medullary cavity. Optionally, alternatively or additionally, the fixation means are configured to fixate the subacromial spacer to an intramedullary fixator implanted or configured for implantation in the humeral medullary cavity. In some embodiments, the intramedullary fixator includes a proximal humeral nail, either a long nail or a short nail. Optionally, additionally or alternatively, the proximal humeral nail is readily provided in a humeral medullary cavity upon or before implanting the prosthesis or subacromial spacer.

In some embodiments, the fixation means comprise a portion or a member, optionally an elongated member, sized to snugly fit in a medullary cavity of the humerus or a slightly reamed segment in the medullary cavity, or optionally change in size, selectively or predeterminately, to anchor or fixate thereinside. In some embodiments, the elongated member includes at least lateral opening configured for lateral fixation by at least one locking screw. In some embodiments, the fixation means include threading or bolting configuration and for example may be sized to thread into a proximal opening of a proximal humeral nail. Optionally, alternatively or additionally, the fixation means include an expandable member or portion, optionally an inflatable member or portion. In some embodiments, such an expandable member or portion is configured for selectively expanding to anchor and/or fasten in the humeral medullary cavity. Optionally, alternatively or additionally, the expandable member or portion is configured for selectively expanding to anchor and/or fasten to the intramedullary fixator (e.g., the proximal humeral nail).

In some embodiments, the prosthesis includes a spring element allowing relative axial motion between the subacromial spacer and the fixation means, optionally over a predetermined threshold weight. In some embodiments, the prosthesis is provided as a monoblock comprising a subacromial spacing portion and an intramedullary fixator portion. In some embodiments, the subacromial spacer is formed of a different material than of the fixation means, being at least one of: plastic, metal, ceramic or any combination thereof, such as metal-backed polyethylene. Optionally parts or members of the prosthesis are glued or adhered one to the other and/or to adjacent bony tissue, optionally by using a bone cement such as PMMA based cement.

In some embodiments, the prosthesis is provided in a surgical kit, also comprising a proximal humeral nail. In some embodiments, the fixation means of the prosthesis, which may be part of the prosthesis, and which may be provided readily connected to the prosthesis or detached therefrom, are connectable into a proximal opening of the proximal humeral nail also provided in the kit. In some embodiments, the kit also includes at least one locking screw which is adapted to travel through a corresponding lateral opening in the proximal humeral nail. In some embodiments, the surgical kit includes a nail guide configured to guide at least one locking screw in at least one orientation to a corresponding at least one lateral opening in the proximal humeral nail.

In an aspect of some embodiments, there is provided a method comprising at least one of the following steps (not necessarily in same order):

1. Creating a percutaneous passage from an outer-body space to a portion of a humeral head. The percutaneous passage may be made using an incision approach, in which the lateral deltoid is split, optionally with a 2 mm to 50 mm size incision, optionally 10 mm to 30 mm size incision, between the acromion and humeral head edges. An entry portal may be central (i.e., at the apex of the humeral head, optionally centered midway between the biceps groove anteriorly and the posterior humeral head) or lateral (i.e., medial to the tendon insertion and centered midway between the biceps groove anteriorly and the posterior humeral head). In case that the rotator cuff is normally in place, it may be divided to expose a superior portion of the humeral head, and a guide pin or trocar may be placed to provide direct passage between the entry portal and the humeral head. Guide pin or trocar positioning and alignment may be checked using imaging (e.g., fluoroscopy).

2. Removing bony tissue to expose a humeral medullary cavity enclosed in the humeral head and/or to facilitate direct communication between the outer-body space and the humeral medullary cavity. Bonny tissue (including but not limited to cortical bone of the superior portion of the humeral head) may be drilled, reamed, hammered and/or broached into using appropriate surgical tools. Optionally, a wire or a rod are used to measure in the medullary cavity sizes for choosing sized or size changes in a selected prosthesis. The medullary cavity may be reamed, in full, partially or in some portions thereof prior to implantation. In some embodiments, the humeral head is further shaped by removing bony tissue to facilitate matching to a subacromial spacer.

3. Providing a prosthesis comprising a subacromial spacer having a surface. Optionally, the prosthesis includes fixating means connected or connectable with the subacromial spacer. Optionally, the prosthesis is provided as part of a kit, further comprising a proximal humeral nail.

4. Fixating the subacromial spacer to the humeral medullary cavity and/or to an intramedullary fixator implanted or configured for implantation in the humeral medullary cavity. In case that an intramedullary fixator is used, such as an intramedullary nail (e.g., a proximal humeral nail), it is first implanted in the humeral intramedullary cavity. In some embodiments, the intramedullary nail comprises a proximal opening, so that subacromial spacer fixation may include connecting the subacromial spacer to the intramedullary nail in the proximal opening. In some embodiments, a nail guide is first attached to the prosthesis and/or to the intramedullary nail. In some such embodiments, the nail guide is configured to guide at least one locking screw in at least one orientation to a corresponding at least one lateral opening in the intramedullary nail (e.g., proximal humeral nail). In some such embodiments, fixation is accomplished by optionally traveling a locking screw through a corresponding lateral opening in the proximal humeral nail. In case that an intramedullary nail is already implanted before the method starts, and in case that the intramedullary nail is sealed at a proximal opening thereof with a sealing cap, the cap may be removed and the prosthesis may be attached instead into the proximal opening. Optionally, additionally or alternatively, fixation includes administering curable cement, optionally a PMMA type. In some embodiments, fixation includes also connection between parts of a prosthesis, for example, at least two of subacromial spacer member, an intramedullary fixator and an optional interconnecting element.

In some embodiments, before or after fixation in the medullary cavity (the latter is optional especially in case of using an intramedullary nail), the distance between the humeral head and the acromion is chosen. In some embodiments, the surface of the subacromial spacer is contoured to maintain the acromion in the chosen distance to the humeral head upon rotation, particularly during a shoulder full range of motion. In some embodiments, the subacromial spacer is selected in correlating in size according to the distance. Optionally, alternatively or additionally, a size of the prosthesis or of any part or member thereof are changed (e.g., expanded or replaced) in correlation with the distance.

Figure 2:
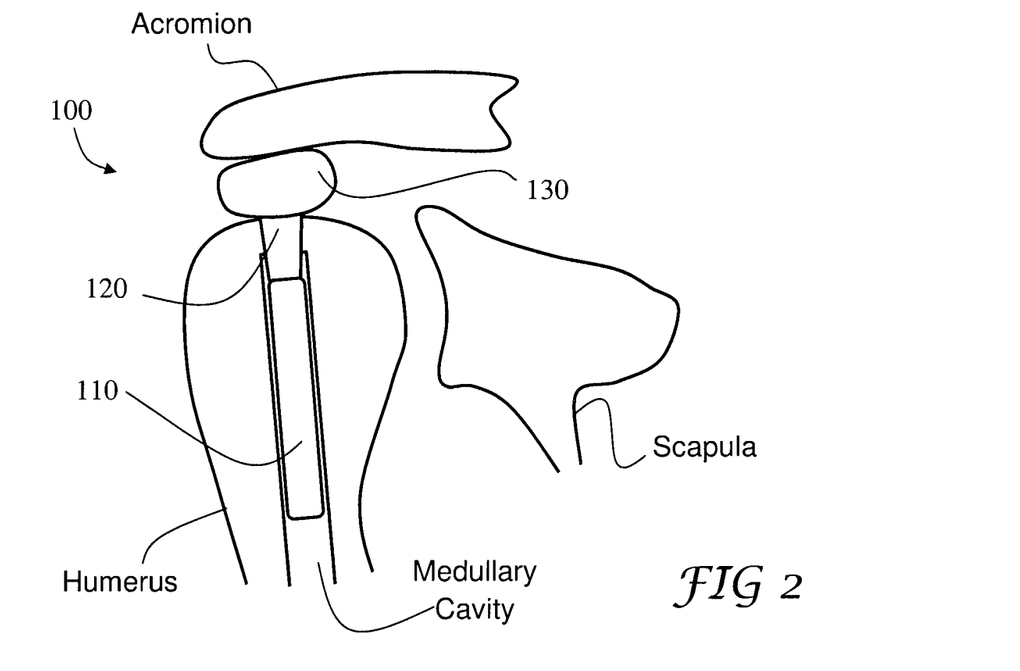
FIG. 2 schematically illustrates an exemplary prosthesis comprising a subacromial spacer, in accordance with some embodiments of the present invention.

Referring to the drawings, FIG. 2 schematically illustrates an exemplary prosthesis 100 shown implanted and deployed in a human shoulder. Prosthesis 100 includes a subacromial spacer 130, an intramedullary fixator 110 and an inner member 120. Prosthesis 100 is implanted through the apex of the humeral head and subacromial spacer 130 is located substantially beneath the acromion at rest (as shown). Subacromial spacer 130 is substantially roundish in cross section and/or includes at least upper surface, shown in contact with the acromion, being contoured (e.g., curved) to allow unhindered motion relative to the acromion when the humerus rotates (e.g., during abduction and adduction). Upper surface of subacromial spacer 130 is elevated and contoured such to maintain a chosen distance between humeral head and acromion at different postures of the humerus relative to acromion and scapula. Optionally, the upper surface is in direct contact partly or throughout an entire shoulder normal or full range of motion. Optionally, upper surface is in direct contact with the acromion, maintaining it is a chosen (e.g., normal) distance, or range of distances, to humeral head during and/or after full abduction followed by a full adduction.

Intramedullary fixator 110 may be any substantially rigid or semi-rigid elongated member shaped and sized to fit in the humeral medullary cavity and fixate prosthesis 100 thereto. Intramedullary fixator 110 may be provided in a fixed size or be expanded or allowed to expand to a chosen size and/or shape, to either loosely or snugly fit in the medullary cavity. If not pressed to anchor or fixate in the medullary cavity, fixator 110 is optionally fixated thereto using auxiliary means such as laterally introduced locking screws. In some embodiments, fixator 110 is an intramedullary nail in the form of or resembling a proximal humeral nail, optionally a short proximal humeral nail being 200 mm or less, optionally 160 mm or less in length. In some embodiments, medullary cavity is slightly reamed, at least along a portion or length segment thereof, for better fitting with fixator 110.

Inner member 120 may be fixedly attached or hingedly or pivotally attached to subacromial spacer 130 at its proximal end and having a distal end connectable (either detachably or permanently) with intramedullary fixator 110. Optionally and alternatively, inner member 120 may be fixedly attached or hingedly or pivotally attached to intramedullary fixator 110 at its proximal end and having a distal end connectable (either detachably or permanently) with subacromial spacer 130. Optionally, alternatively or additionally, inner member 120 is provided disconnected at both ends. Optionally, inner member 120 is picked out of a variety of inner members differentiated by shape and/or size, depending, for example, in chosen distance or range of distances between upper surface of subacromial spacer 130 and proximal end of fixator 110.

Figure 3:
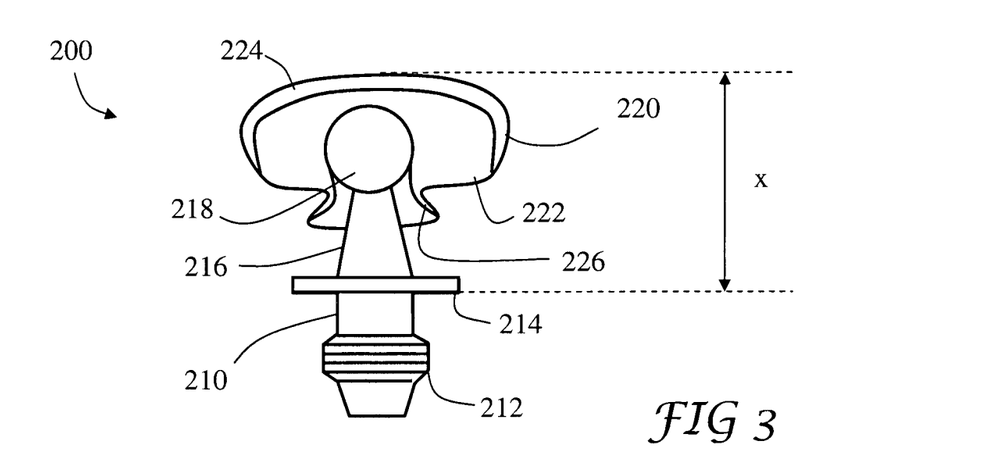
FIG. 3 schematically illustrates an exemplary prosthesis adapted for fixating to a proximal humeral nail, in accordance with some embodiments of the present invention.

Reference is now made to FIG. 3 which schematically illustrates an exemplary prosthesis 200 adapted for fixating to a proximal humeral nail (not shown). Prosthesis 200 implantation may be performed together with proximal humeral nail implantation or to such a nail being readily implanted in a humerus (not shown). Prosthesis 200 includes a fixation member 210 provided in a bipolar articulation with a subacromial spacer member 220, allowing rotation in at least one axis therebetween. Fixation member 210 includes an elongated body sized and configured for partial insertion into a proximal opening in a proximal humeral nail (PHN), and comprising fixation threads or fins 212 in proximity to its distal end, adapted to thread with, press and/or lock onto inner wall portions of the nail. A stopper 214 sets maximal protrusion of prosthesis 100 into a PHN via its proximal opening, hence providing minimal or correct distance x between the superior portion of a humeral head (in which the PHN is implanted) and the upper surface of subacromial spacer member 220. Distance x may be any chosen value between 3 mm and 17 mm, optionally between 6 and 8 mm. An optionally frustum shaped portion 216 emerges proximally from stopper 214 and ends with a hinge 218 having a circular or other roundish cross section (optionally a cylinder or a sphere). Subacromial spacer member 220 includes a curved body 222 acting as a socket to hinge 218 allowing articulated motion around it that is limited by lateral borders 226. An optional covering portion 224 may be provided on top of body 222 and may differ from body 222 by at least one feature and/or material. In some embodiments, covering portion 224 is resilient while body 222 is substantially rigid. Optionally, alternatively or additionally, covering portion 224 has an upper surface configured for continuous contact with an acromion, allowing unhindered slippery motion with it, and comprises a coefficient of friction substantially smaller than of curved body 222.

Figure 4A:
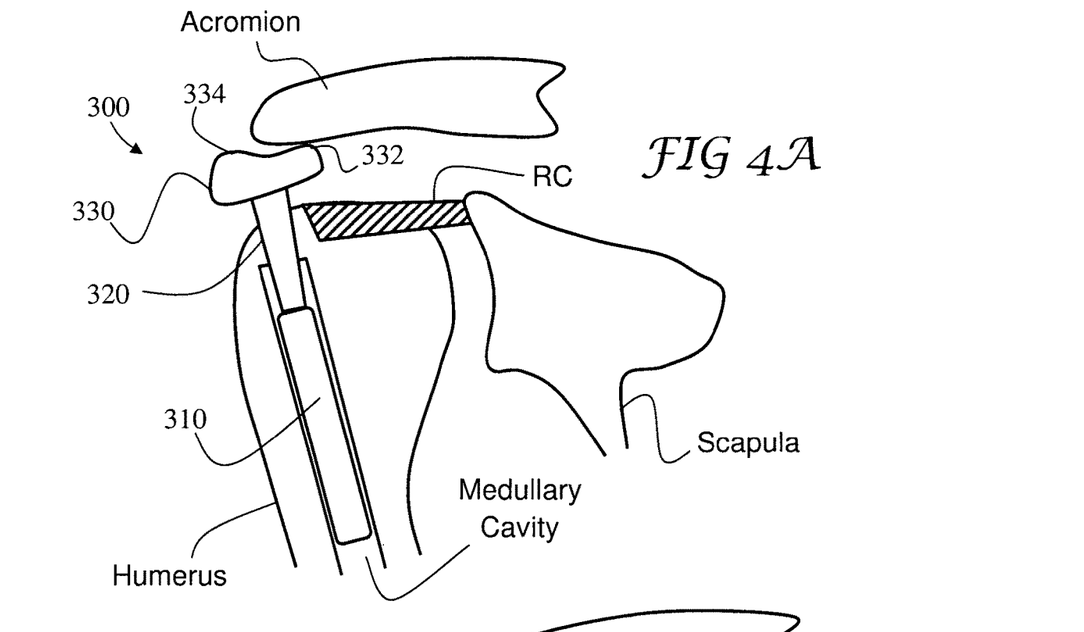
FIGS. 4A-C schematically illustrate an exemplary prosthesis comprising a subacromial spacer configured for greater tubercle introduction, and exemplary features thereof, in accordance with some embodiments of the present invention.
Figures 4B, 4C:
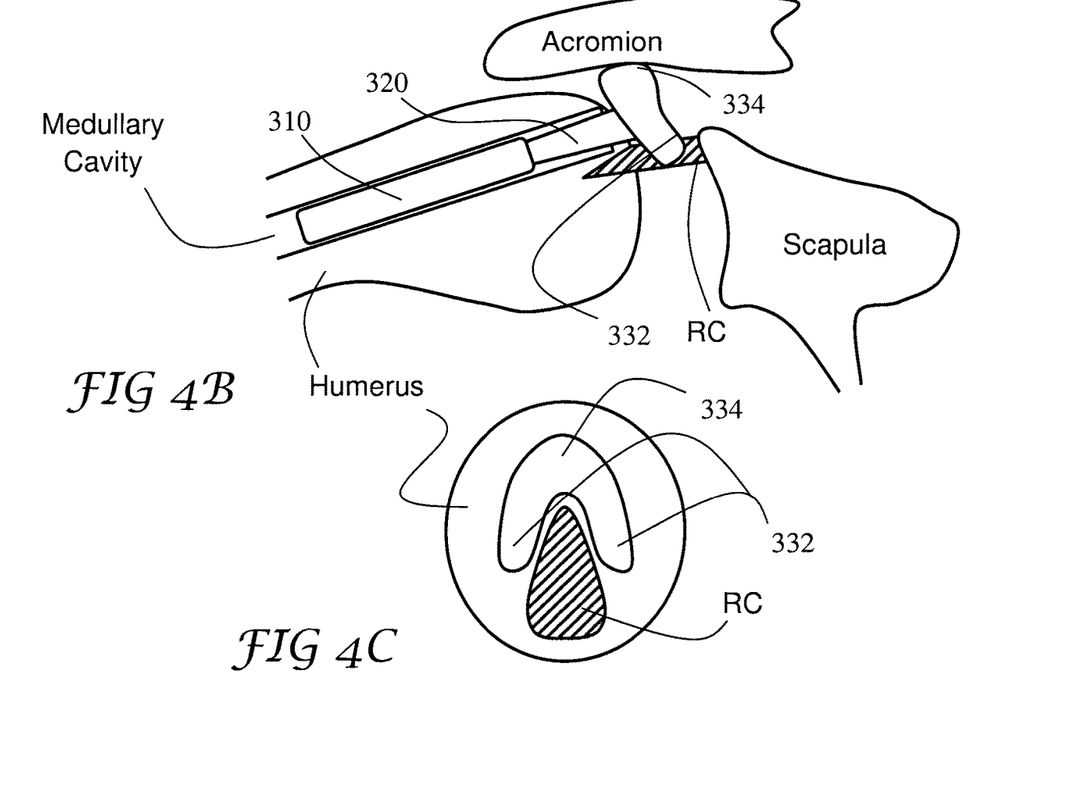

In some embodiments, for example in scenarios where there is a need to implant a subacromial spacer adjacent to a non-torn or partially less-severely torn rotator cuff, a prosthesis including a subacromial spacer part or member may be positioned and/or shaped such to avoid harm and interference with rotator cuff integrity and/or function. FIGS. 4A-C schematically illustrate an exemplary prosthesis 300 configured for greater tubercle introduction. In FIG. 4A prosthesis 300 is shown in a substantially medial humerus position whereas in FIG. 4B it is shown in a substantially lateral humerus position. Prosthesis 300 includes an intramedullary fixator 310 sized and/or configured for implantation in a medullary cavity of a human humerus, a subacromial spacer member 330 and an inner member 320. In some embodiments, intramedullary fixator 310 is a short or a long proximal humeral nail. Fixator 310 may be inserted through a central entry point located at the top of the humeral head or it may be inserted through a lateral entry point located inside the greater tubercle. As such, intramedullary fixator 310 may be traveled through or adjacent rotator cuff RC. Optionally and alternatively, intramedullary fixator 310 is introduced through a different entry point, optionally allowing bypass to RC.

Subacromial spacer 330 is sized and shaped to maintain direct contact with acromion and/or a chosen distance or range of distances between humeral head and acromion at most or any humerus positioning. In some embodiments, inner member 320 projects from the humerus laterally to the humeral head and in some such embodiments, subacromial spacer 330 may be contoured and/or lengthened to facilitate contact with the acromion at a full medial humerus positioning. A shown, subacromial spacer 330 includes a medial upper portion 332 and a lateral upper portion 334 configured such that at substantial medial humerus position portion 332 is in contact with the acromion, and at substantial lateral humerus position portion 334 is in direct contact with the acromion. As such, subacromial spacer 330 may be considered a cam-like member sized and shaped to convert humerus circular motion to linear motion and/or to maintain distance or range of distances relatively between humeral head and acromion. In some occasions where, for example in a substantial lateral humerus positioning (as shown in FIG. 4B), subacromial spacer 330 travels across the periphery of rotator cuff RC, it may be provided in a shaped and configured also to avoid actual contact with RC throughout its entire travel. FIG. 4C shows an upward cross section of subacromial spacer 330 and RC when humerus is at lateral position; as shown, subacromial spacer 330 has an inverted U-shaped cross section having medial upper portion 332 divided into two contact portions enclosing a void sized and shaped to accommodate RC with no direct contact with its boundaries.

Figure 5A:
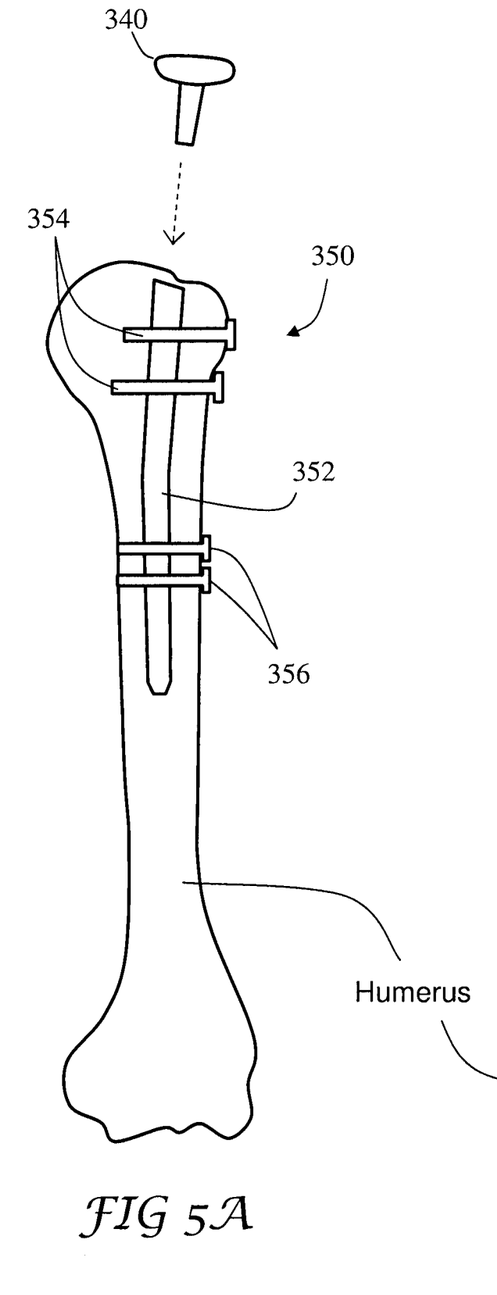
FIGS. 5A-B schematically illustrate an exemplary prosthesis comprising a subacromial spacer connectable to a short PH nail and a long PH nail, respectively, in accordance with some embodiments of the present invention.
Figure 5B:
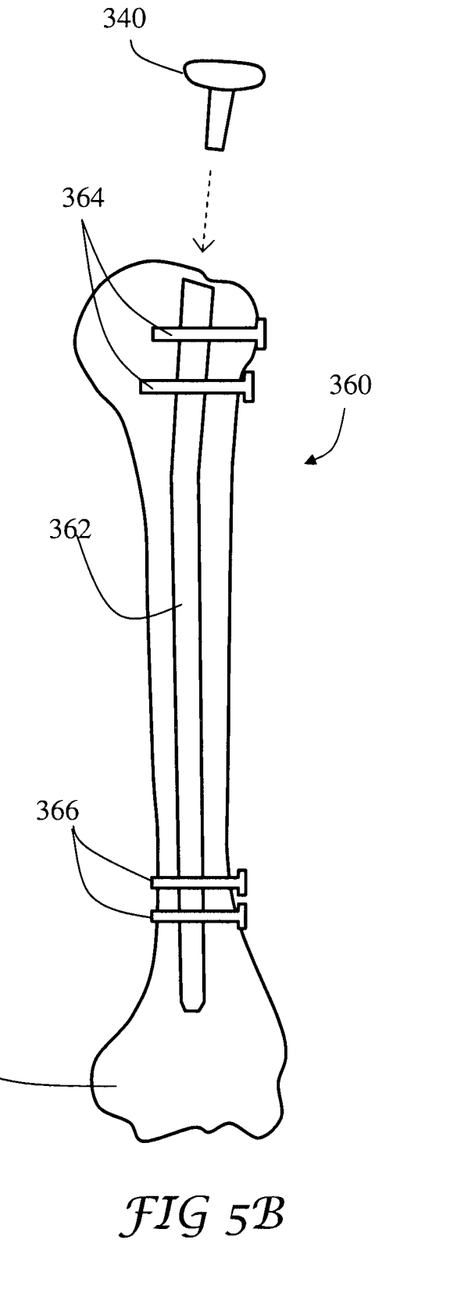

Reference is now made to FIGS. 5A-B which schematically illustrate prosthesis 340 connectable to a short proximal humeral (PH) nail system 350 and a long PH nail system 360, respectively. Nail system 350 includes a short PH nail 352, a plurality of proximal lock screws 354 and a plurality of distal lock screws 356. Nail system 360 includes a long PH nail 362, a plurality of proximal lock screws 364 and a plurality of distal lock screws 366. Either nail system 350 or nail system 360 may be provided with prosthesis 340, optionally in a single kit, or may be readily implanted in the humerus before or during prosthesis 340 implantation procedure. In some embodiments, the choice between a short or a long PH nail relates to the condition of the humerus, whether it is intact, fractured and/or osteoporotic (or otherwise ill). Prosthesis 340 may be similar or identical to prosthesis 200 in the sense it includes a subacromial spacer member and a connection member for connecting with an intramedullary nail.

Figure 6A:
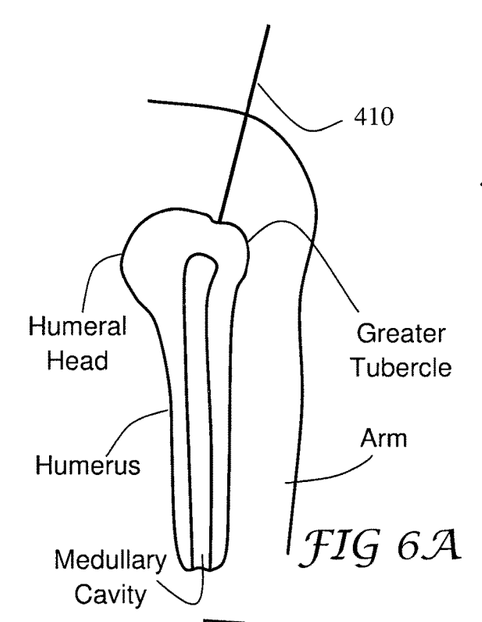
FIGS. 6A-F schematically illustrate steps in a method for implanting an exemplary prosthesis and an intramedullary fixator in a humerus, in accordance with some embodiments of the present invention.

Reference is made to FIGS. 6A-F which schematically illustrate steps in a method for implanting an exemplary prosthesis 460 and an intramedullary fixator 440 in a humerus. A patient's arm enclosing a humerus is shown in part and in cross section. A surgical kit 400 is used comprising at least one of a guide pin 410, a drill 420, a delivery apparatus 430, intramedullary fixator 440, a guide 450 and prosthesis 460 optionally provided as separated connectable inner member 462 and subacromial spacer member 464. As shown in FIG. 6A, guide pin 410 is first used for creating a percutaneous passage from outside the arm to the humeral head, optionally through the lateral deltoid and/or the rotator cuff (not shown). An entry portal to the arm may be central or lateral. Positioning and/or alignment of guide pin 410 may be then checked using imaging (e.g., fluoroscopy).

Figure 6B:
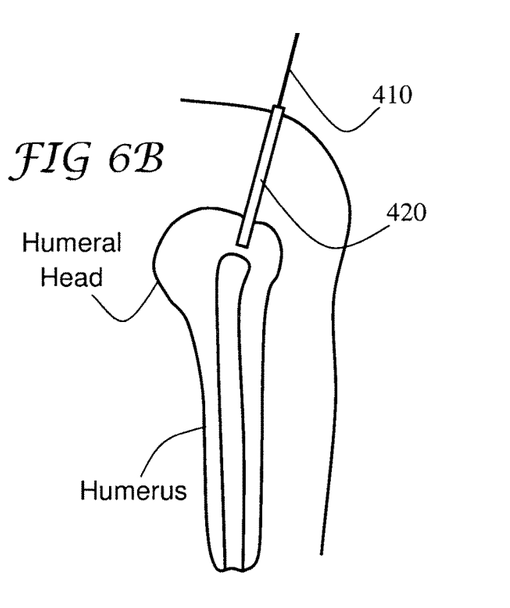
Figure 6C:
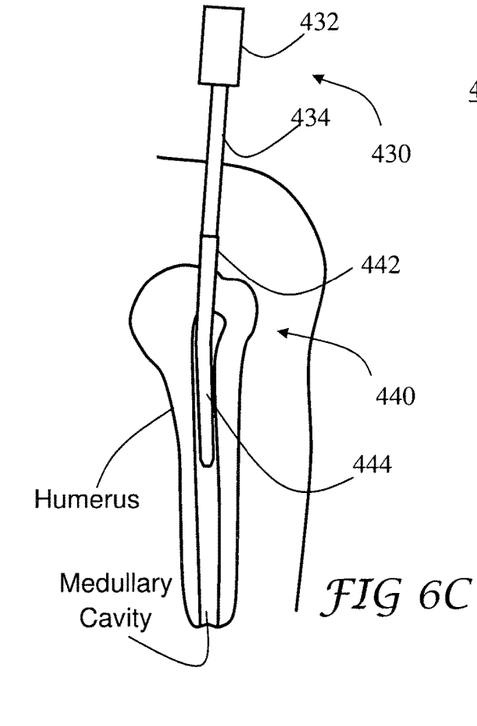

As shown in FIG. 6B, drill 420 is introduced and directed towards a target point at humeral head boundary. In some embodiments and as shown in the figure, drill 420 includes a lumen used to pass over and along guide pin 410. Drill 420 is then used to drill through humeral head and remove bony tissue at least until reaching humeral medullary cavity, optionally exposing it for an implantation therein. Next, as shown in FIG. 6C, intramedullary fixator 440 is implanted in the medullary cavity. Intramedullary fixator 440 is optionally a short PH nail which comprises an elongated body 444, optionally slightly bent as commonly known in current commercially available PH nail systems, optionally for easing lateral introductions. A proximal portion 442 in fixator 440 is hollow and ends with a proximal opening at its top. Proximal portion 442 is connected, optionally threaded, to delivery apparatus 430 when fixator 440 is introduced and deployed. Although not shown, delivery apparatus 430 may be applied while connected to guide 450. Delivery apparatus 430 includes a distal member 434 configured for delivering in patient's arm and a proximal member 432 configured for connecting with guide 450. Optionally, proximal member 432 and distal member 434 are hollow and allow introduction of parts therethrough from outside the arm and into fixator 440 and/or medullary cavity, when deployed. Optionally, distal member 434 includes connection means (e.g., thread, snap-lock, nut or bolt, etc.) to outside boundaries of proximal portion 442 of fixator 440, and/or to inner boundaries thereof. For implanting fixator 440 in the medullary cavity, a hammer or other pushing or pressing means are used to force it in place.

Figure 6D:
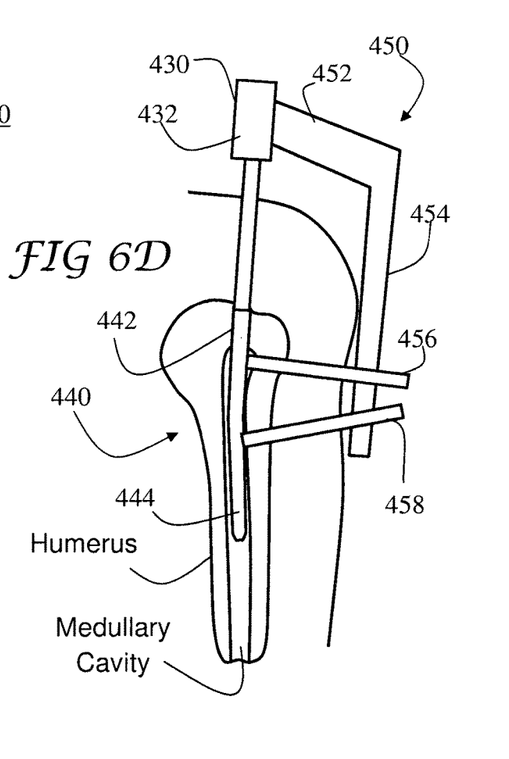
Figure 6E:
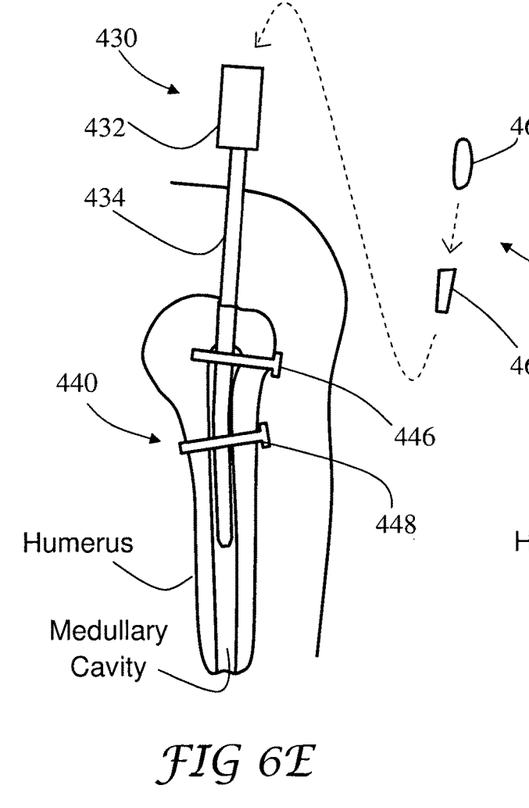

As shown in FIG. 6D, once in place, guide 450 is connected to delivery apparatus 430 and is used for locking fixator 440 in the medullary cavity using lateral locking screws. Guide 450 includes a leg 454 with openings and an extension 452 detachably connectable to proximal member 432 of delivery apparatus 430. When fixator 440 is correctly in place and connected with delivery apparatus 430 and guide 450, a plurality of lateral channels, including a proximal channel 456 and a distal channel 458, are introduced through the openings of leg 454 and through the arm thereby creating passages until humerus. Drills or other means are introduced (not shown) via channels 456 and 458 and utilized to create lateral openings in the humerus towards medullary cavity, until reaching corresponding lateral openings in elongated body 444 of fixator 440. As shown in FIG. 6E, a plurality of locking screws, including a proximal locking screw 446 and a distal locking screw 448, are provided at least partially across the humerus and through corresponding lateral openings in fixator 440 and locking fixator 440 in the medullary cavity. After placement of the locking screws, guide 450 is removed.

Figure 6F:
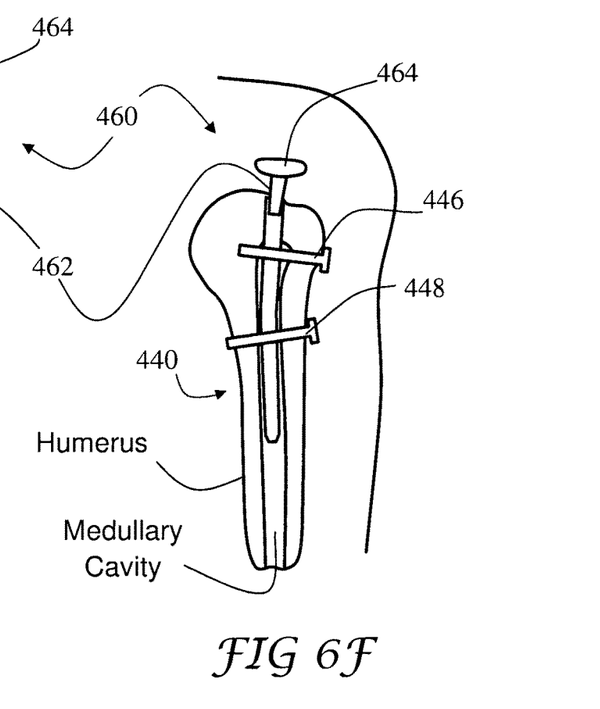

Delivery apparatus 430 is optionally used then to deliver members of prosthesis 460 into the subacromial space and to connect with fixator 440. Optionally and alternatively, delivery apparatus 430 is first removed and only after prosthesis 460 and/or members thereof are delivered via the previously made percutaneous channel and at least partly occupied with delivery apparatus 430. In some embodiments, inner member 462 and subacromial spacer member 464 are delivered separately and sequentially, so at first inner member 462 is connected to fixator 440 (optionally in its proximal opening) and then subacromial spacer member 464 is delivered and connected to inner member 462. Optionally and alternatively, both members are delivered connected, optionally in lower or even lowest profile. In some embodiments, optionally in any of the two delivery options described above, subacromial spacer member 464 is delivered at lower profile, optionally having its longitudinal axis substantially coinciding with longitudinal axis of delivery apparatus 430 and/or of fixator 440. FIG. 6F shows prosthesis 460 fully deployed with intramedullary fixator 440 locked in medullary cavity with locking screws 446 and 448.

Figure 7:
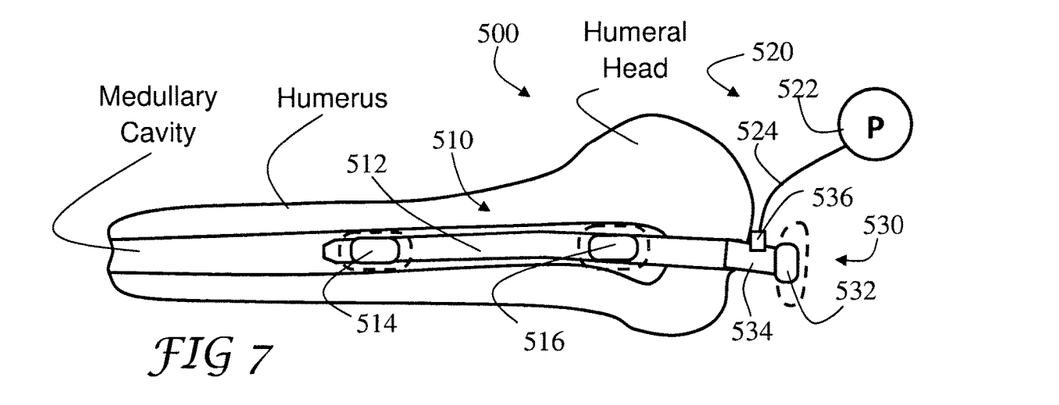
FIG. 7 schematically illustrates an exemplary prosthesis comprising an expandable subacromial spacer, in accordance with some embodiments of the present invention.

Reference is now made to FIG. 7 which schematically illustrates an exemplary prosthesis 500. Prosthesis 500 is shown in a partially illustrated humerus having a humeral head and a medullary cavity. Prosthesis 500 includes an intramedullary fixator 510 provided connected or connectable with an expandable subacromial spacer 530. Subacromial spacer 530 includes an expandable spacer member 532 connected to a non-expandable inner member 534 shown connected to fixator 510. In some embodiments, expandable spacer member is inflatable, optionally by liquid (e.g., saline) or by gas (e.g., air), or optionally by other flowable materials, including but not limited to gels, hyaluronic acid, curable materials or others. In some such embodiments, subacromial spacer 530 includes an inflation port 536 connectable to an inflation system 520 comprises a pressurized or pressuring member 522, optionally filled with an inflation medium or connectable with an inflation medium reservoir (not shown), and an interconnecting line 524 allowing a pressurized inflation medium flowing therein from member 522 to inflation port 536. In some embodiments, intramedullary fixator 510 is a rigid non-expandable type intramedullary nail as described in previous disclosures. Optionally and alternatively, fixator 510 includes at least one expandable (e.g., inflatable) portion, such as a distal expandable portion 514 and a proximal expandable portion 516, allowing it to anchor and/or press to adjacent medullary cavity wall portions. Advantages of using expandable portions instead of locking screws may include less harm to humerus and other body tissues during operation, less healing/hospitalization time and possibility to match different diameters and cross sections of medullary cavities in different humerus bones. In some embodiments, portion 514 and/or 516 is rigid enough to force shaped deformation to at least one of adjacent marrow and/or spongy bone tissues and/or cortical bone tissues. Optionally and alternatively, portion 514 and/or 516 is flexible enough to conform to local shape imposed by spongy bone tissues and/or compact bone tissues. In some embodiments, portions 514 and 516 are fluidly communicating with an inflation port, either inflation port 536 or a different one (not shown).

Figures 8A, 8B:
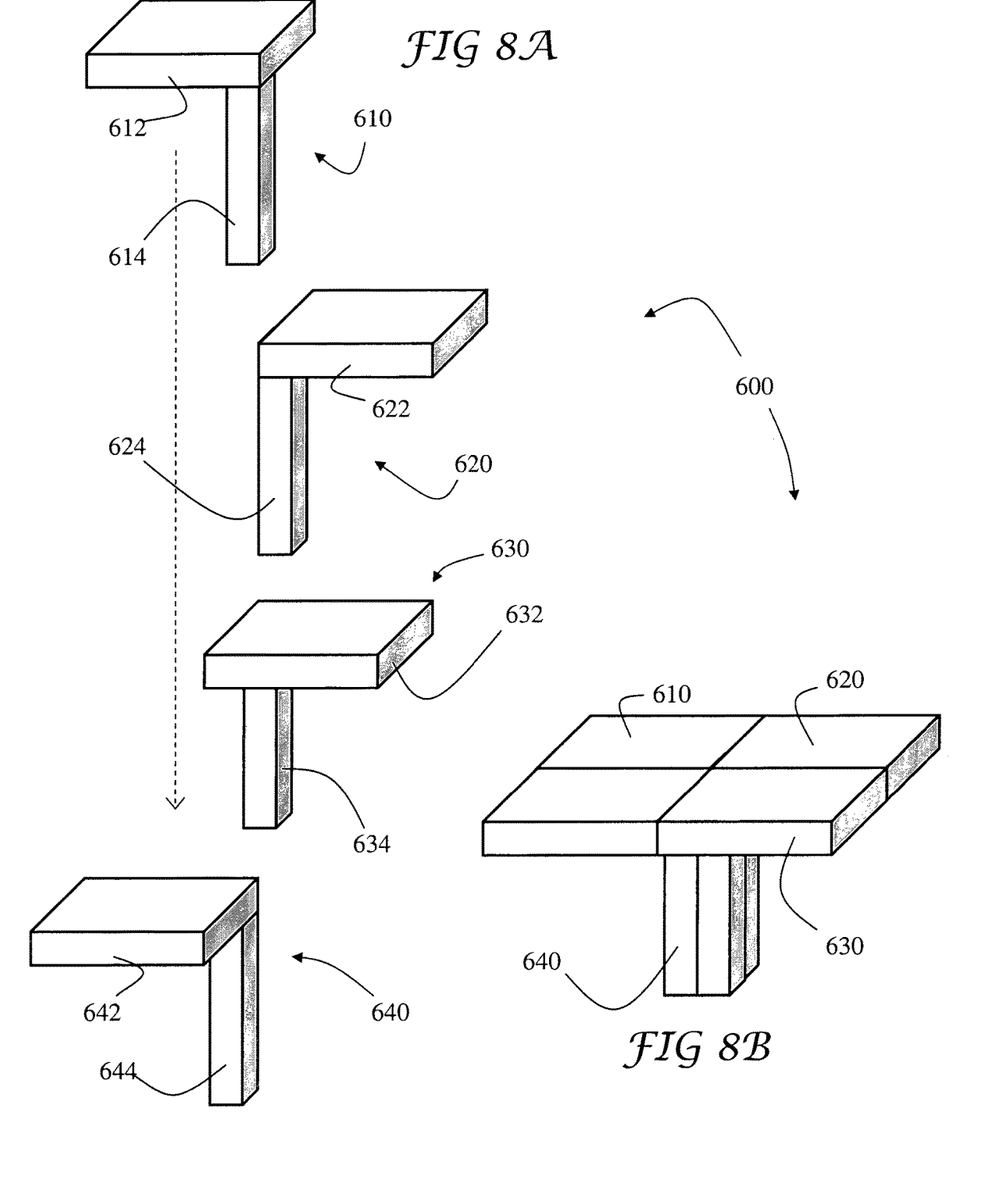
FIGS. 8A-B schematically illustrate an exemplary subacromial spacer assembly, in accordance with some embodiments of the present invention.

In some embodiments, the prosthesis or any of its members or parts (e.g., a subacromial spacer member) are delivered disassembled sequentially to a target in-body location and are assembled in-place. Advantages of such prostheses may include a smaller entry portal and delivery passage from outside the body to the humeral head and other advantages of minimally invasive procedures. FIGS. 8A-B schematically illustrate an exemplary subacromial spacer assembly 600, which includes four interconnectable members 610, 620, 630 and 640, although it may include any number of interconnectable members of different sizes and shapes according to need and design efficiency. Any of the members include a solid having an upper contact surface (surface 612 in member 610, surface 622 in member 620, surface 632 in member 630 and surface 642 in member 640) configured for providing a contact portion for maintaining a continuous direct contact with the acromion and/or a chosen distance or range of distances between humeral head and acromion, when correctly deployed to an intramedullary fixator (not shown) readily implanted in a humeral medullary cavity. Any of the members include a perpendicular extension downwardly arising from a corner of the solid (extension 614 in member 610, extension 624 in member 620, extension 634 in member 630 and extension 644 in member 640) configured to assemble together with rest of extensions into a single leg connectable with an intramedullary fixator.

Figures 9A, 9B:
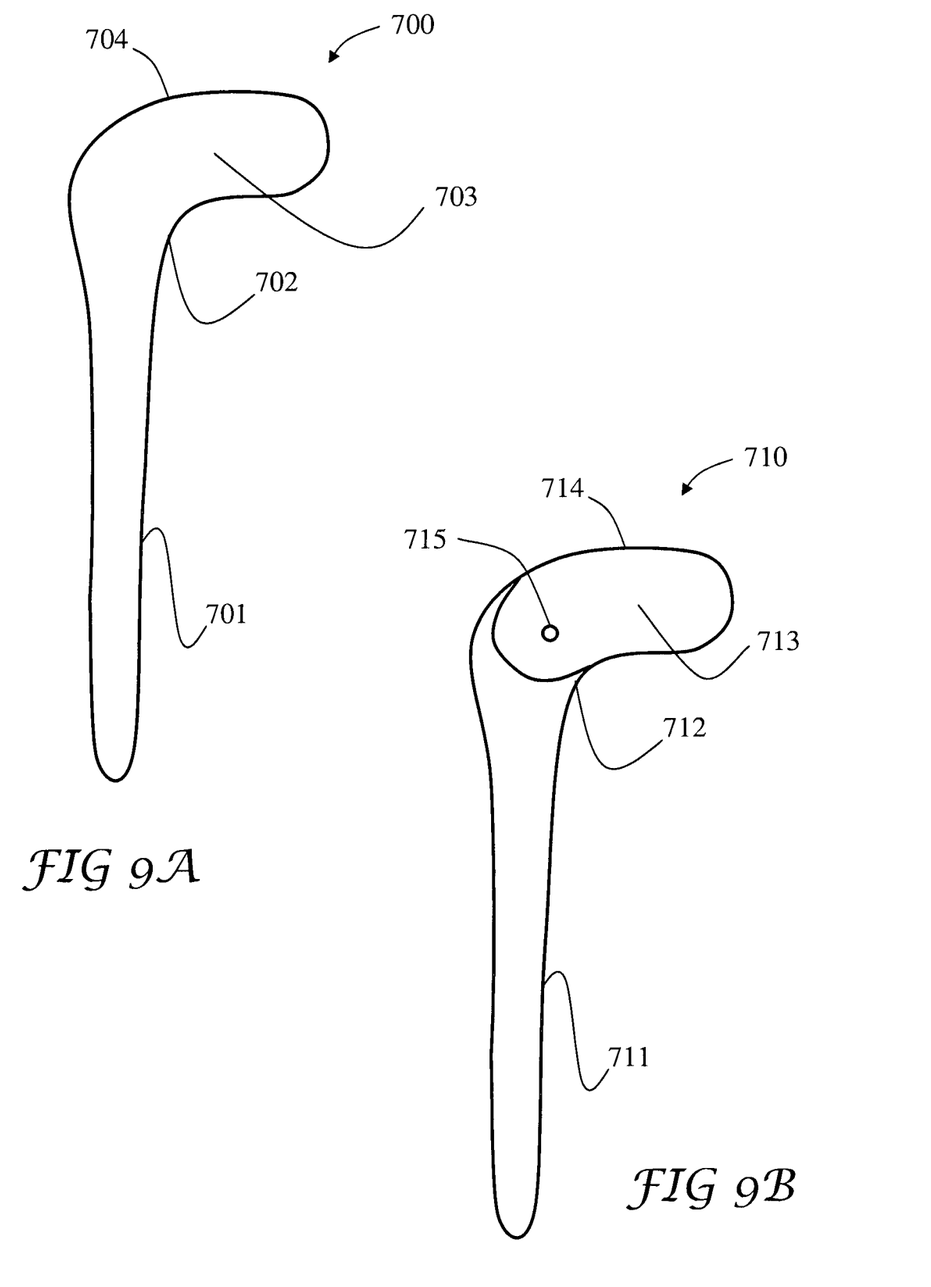
FIGS. 9A-B schematically illustrate other exemplary prostheses, in accordance with some embodiments of the present invention.

Reference is now made to FIG. 9A which schematically illustrates a monoblock type prosthesis 700 which is unitary formed and shaped such to include an intramedullary fixation portion 701 and a subacromial spacer portion 703. A neck portion 702 separates between fixation portion 701 and spacer portion 703 and is configured to be positioned adjacent outer surface of the humeral head upon implantation. Spacer portion 703 includes an upper surface 704 shaped and sized for continuous contact with an acromion when implanted in a humerus.

FIG. 9B shows another exemplary prosthesis 710 being optionally similar in overall deployment shape to monoblock prosthesis 700, having similar intramedullary fixation member 711 and a neck portion 712. A subacromial spacer member 713 having an upper contact surface 714 is pivotally fixated to fixation member 711 adjacent neck portion 712, optionally to ease maneuvering and delivery of prosthesis 710 in the body. Optionally, a spring (not shown) is provided in between subacromial spacer member 713 and fixation member 711 so that the shown form may be set as a normally unbiased form (i.e., when no external forces are applied to stretch such a spring).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method comprising:
   creating a percutaneous passage from an outer-body space to a portion of a humeral head;
   removing bony tissue from the humeral head to facilitate direct communication between the outer-body space and a humeral medullary cavity enclosed in the humeral head;
   providing a prosthesis comprising a stretchable subacromial spacer, the subacromial spacer having a lateral upper portion and a medial upper portion; and
   fixating the subacromial spacer to at least one of the humeral medullary cavity and an intramedullary fixator, the subacromial spacer being sized and shaped to maintain direct contact with an acromion such that only the lateral upper portion directly contacts the acromion at a substantially lateral humerus position and only the medial upper portion directly contacts the acromion at a substantially medial humerus position, the intramedullary fixator being implanted in the humeral medullary cavity.

2. The method of claim 1, further comprising:
   implanting an intramedullary nail in the humeral intramedullary cavity, the intramedullary nail comprising a proximal opening;
   wherein the fixating comprises connecting the subacromial spacer to the intramedullary nail in the proximal opening.

3. The method of claim 2, further comprising:
   attaching a nail guide to the prosthesis, the nail guide configured to guide at least one locking screw in at least one orientation to a corresponding at least one lateral opening in the proximal humeral nail; and
   traveling a locking screw through a corresponding lateral opening in the proximal humeral nail.

4. The method of claim 1, wherein the fixating includes administering curable cement.

5. A method comprising:
   providing a prosthesis comprising a subacromial spacer having a resilient portion and a rigid portion, the resilient portion comprising a lateral upper portion and a medial upper portion; and
   securing the prosthesis between a humeral head of a humerus and an acromion such that the resilient portion contacts the acromion, wherein a only the lateral upper portion directly contacts the acromion at a substantially lateral humerus position and only the medial upper portion directly contacts the acromion at a substantially medial humerus position to allow unhindered motion of the acromion relative to the humerus.

6. The method of claim 5, wherein the step of securing the prosthesis includes a step of fixating the prosthesis to at least one of a humeral medullar cavity and an intramedullary fixator, the intramedullary fixator being implanted in the humeral medullar cavity.

7. The method of claim 6, further including the step of implanting an intramedullary nail comprising a proximal opening, wherein the step of fixating the prosthesis includes connecting the prosthesis to the intramedullary nail in the proximal opening.

8. The method of claim 7, further comprising:
attaching a nail guide to the prosthesis, the nail guide configured to guide at least one locking screw in at least one orientation to a corresponding at least one lateral opening in the proximal humeral nail, and
traveling a locking screw through a corresponding lateral opening in the proximal humeral nail.

9. The method of claim 6, wherein the fixating includes administering curable cement.

10. The method of claim 5, further including the step of accessing the proximal humerus by creating a percutaneous passage from an outer-body space to the proximal humerus.

11. The method of claim 10, further including the step of providing direct communication between the outer-body space and a humeral medullary cavity by removing bony tissue.

12. The method of claim 5, wherein the step of providing a prosthesis includes providing a subacromial spacer with a curved rigid body having lateral borders.

13. The method of claim 12, wherein the step of providing a prosthesis includes providing a subacromial spacer with a hinge such that the curved rigid body acts as a socket to the hinge to allow articulated motion of the curved rigid body.

14. The method of claim 13, wherein the articulated motion of the curved rigid body is limited by the lateral borders.

15. A method comprising:
providing a prosthesis comprising a subacromial spacer having a resilient portion, the resilient portion comprising any of a malleable, elastic, plastic, expandable, compressible, and stretchable material, the resilient portion comprising a lateral upper portion and a medial upper portion; and
securing the prosthesis to a proximal humerus so that the subacromial spacer is positioned between a humeral head such that only the lateral upper portion directly contacts the acromion at a substantially lateral humerus position and only the medial upper portion directly contacts the acromion at a substantially medial humerus position to allow motion of the humerus relative to the acromion.

* * * * *